United States Patent [19]
Nakagome et al.

[11] 3,963,736
[45] June 15, 1976

[54] PREPARATION OF 1-(LOWER ALKYL)-1,4-DIHYDRO-7-METHYL-4-OXO-1,8-NAPHTHYRIDINE-3-CARBOXYLIC ACIDS

[75] Inventors: Takenari Nakagome, Toyonaka; Hideo Agui, Minoo; Toru Mitani, Nishinomiya; Mitsuo Nakashita, Kobe, all of Japan

[73] Assignee: Sumitomo Chemical Company, Limited, Osaka, Japan

[22] Filed: June 10, 1974

[21] Appl. No.: 478,118

Related U.S. Application Data

[62] Division of Ser. No. 110,586, Jan. 18, 1971, Pat. No. 3,849,421.

[30] Foreign Application Priority Data

| Jan. 28, 1970 | Japan | 45-7895 |
|---|---|---|
| Feb. 18, 1970 | Japan | 45-14355 |
| Feb. 23, 1970 | Japan | 45-15721 |
| Feb. 24, 1970 | Japan | 45-16004 |
| Feb. 24, 1970 | Japan | 45-16005 |

[52] U.S. Cl. ............................ 260/295.5 B
[51] Int. Cl.² ........................... C07D 471/04
[58] Field of Search ................. 260/295.5 B

[56] References Cited
UNITED STATES PATENTS

| 3,673,193 | 6/1972 | Lesher et al. | 260/295.5 B |
|---|---|---|---|
| 3,855,232 | 12/1974 | Brundage et al. | 260/295.5 B |

*Primary Examiner*—Natalie Trousof
*Assistant Examiner*—Bernard I. Dentz
*Attorney, Agent, or Firm*—Sughrue, Rothwell, Mion, Zinn & Macpeak

[57] ABSTRACT

A process for producing a compound of the formula:

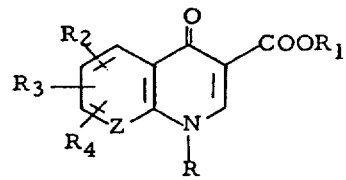

wherein Z is CH or N; R is a lower alkyl group, a lower alkenyl group, a cycloalkyl group or a hydroxyalkyl group; $R_1$ is a hydrogen atom or lower alkyl group; when Z is N, $R_2$, $R_3$ and $R_4$ are a hydrogen atom, a halogen atom a lower alkyl group, a lower alkoxyl group, a lower hydroxyalkyl group, a lower acyloxyalkyl group, trihalogenoalkyl group, a carboxyl group, a cyano group, or an aralkyl group; when Z is CH, $R_2$, $R_3$ and $R_4$ are a hydrogen atom, a halogen atom, a lower alkyl group, a lower alkoxyl group, a trihalogenoalkyl group, a cyano group, a nitro group, an alkylmercapto group, a lower alkylenedioxy group, or a lower alkylene bridge attached to the quinoline nucleus, which comprises heating a compound of the formula

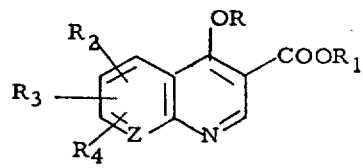

wherein R, $R_1$, $R_2$, $R_3$, $R_4$ and Z are as defined above, followed, if desired, by hydrolyzing the product obtained, is disclosed.

The product is useful as an antibacterial agent. An intermediate having the formula:

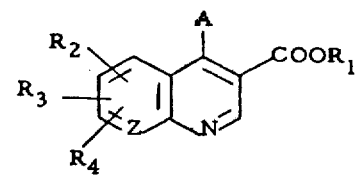

wherein A is OR or a halogen atom, and R, $R_1$, $R_2$, $R_3$, $R_4$ and Z are as defined above, and a process for its preparation are also disclosed.

11 Claims, No Drawings

PREPARATION OF 1-(LOWER ALKYL)-1,4-DIHYDRO-7-METHYL-4-OXO-1,8-NAPHTHYRIDINE-3-CARBOXYLIC ACIDS

This is a division of application Ser. No. 110,586, filed Jan. 18, 1971, now U.S. Pat. No. 3,849,421.

SUMMARY OF THE INVENTION

The present invention relates to a novel process for producing a compound represented by the general formula:

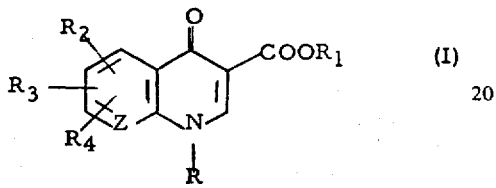

wherein Z represents CH or N; R represents a lower alkyl group, a lower alkenyl group, a cycloalkyl group, or a hydroxyalkyl group; $R_1$ represents a hydrogen atom or a lower alkyl group; and when Z is N, $R_2$, $R_3$ and $R_4$, which may be the same or different, represent a hydrogen atom, a halogen atom, a lower alkyl group, a lower alkoxyl group, a lower hydroxyalkyl group, a lower acyloxyalkyl group, a trihalogenoalkyl group, a carboxyl group, a cyano group, an aralkyl group, or an aralkenyl group; said hydrogen atom and each group being substituted on the naphthyridine nucleus; and when Z is CH, $R_2$, $R_3$ and $R_4$, which may be the same or different, represent a hydrogen atom, a halogen atom, a lower alkyl group, a lower alkoxyl group, a trihalogenoalkyl group, a cyano group, a nitro group, an alkylmercapto group, a lower alkylenedioxy group or a lower alkylene bridge attached to the 6- and 7-, or the 7- and 8-positions of the quinoline nucleus.

The present invention also relates to a compound which is an intermediate for the above-described compound, represented by the general formula:

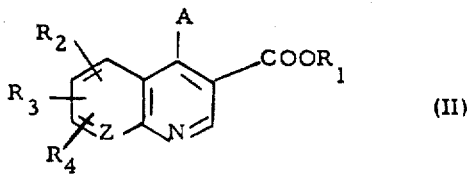

wherein A represents OR or a halogen atom and Z, R, $R_1$, $R_2$, $R_3$ and $R_4$ each have the same meanings as described in the general formula (I) and a process for the production of the intermediate (II).

DETAILED DESCRIPTION OF THE INVENTION

The term "lower alkyl", as used throughout the present specification, is intended to encompass alkyl radicals having from one to four carbon atoms which can be straight or branched chained, and the term "lower alkenyl" is intended to encompass alkenyl radicals up to four carbon atoms.

Accordingly, the first object of the present invention is to provide an advantageous process for the production of a compound represented by the general formula (I).

Another object is to provide a novel intermediate for the abovedescribed compound represented by the formula (II).

A further object is to provide a process for producing intermediate (II).

Other objects and merits of this invention will be apparent from the following description.

The compound (I) is produced by heating a compound represented by the general formula:

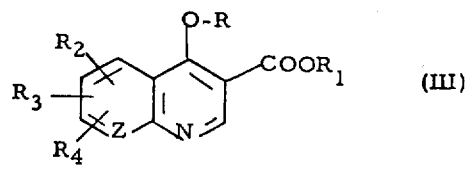

wherein Z, R, $R_1$, $R_2$, $R_3$ and $R_4$ are as defined in general formula (I) in the presence or absence of an acid catalyst or an alkylating agent and further hydrolyzing the product so obtained.

The 1-substituted 4-oxo derivative represented by the general formula (I) has hitherto been prepared by alkylating a 4-hydroxy derivative represented by the general formula:

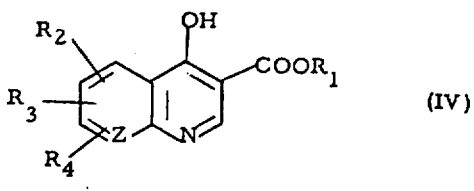

wherein Z, $R_1$, $R_2$, $R_3$ and $R_4$ are as defined in general formula (I) or further hydrolyzing the alkylation product. However, this conventional process is accompanied by the disadvantages that an expensive reagent, such as an alkyl iodide or an alkyl bromide, or a reagent which is very toxic and difficult to handle, such as dimethyl sulfate, diethyl sulfate and sodium hydride, is consumed in extremely large quantities in the alkylation reaction and the yield for the product is generally low.

As the results of various investigations the present inventors have discovered an industrially profitable process for producing the desired compound in a high yield without the consumption or loss of such expensive or troublesome reagents.

In the above process of the present invention, the alkyl group R of the 4-alkyloxy derivative represented by the general formula (III) undergoes rearrangement to the ring nitrogen atom at the 1-position, whereby the 1-substituted 4-oxo derivative represented by the general formula (I) is formed. For rearrangement, the starting material can simply be melted upon heating, but a solvent inert to the reaction, such as toluene, benzene, xylene, diphenyl, diphenyl ether, a mineral oil, a petroleum hydrocarbon, an alcohol, dioxane, dimethyl formamide, a halogenated hydrocarbon or a mixture thereof can be employed. The reaction is conducted at a temperature of from 50°C to 300°C, and preferably from 100°C to 250°C. The reaction can proceed by heating either in the absence of a solvent or in the presence of a solvent, but when the reaction is conducted in the presence of an alkylating agent such as an alkyl halide, an alkenyl halide, a cycloalkyl halide, a hydroxy alkyl halide, a dialkyl sulfate, an alkyl p-toluenesulfonate, or triethyloxonium fluoroborate or in the presence of an acid catalyst, the reaction is markedly promoted and the desired compound can be obtained in high yields, even under mild conditions.

As acid catalysts which can be used in the above reaction, inorganic acids, such as a hydrogen halide, organic acids, such as p-toluenesulfonic acid or acetic acid, and Lewis acids such as aluminum chloride or a boron trifluoride are applicable.

The amount of the material used in promoting the reaction is not limiting. It is preferable to use from 1 to 1/1000 equivalent amount of the acid catalyst or the alkylating agent. Use of a larger amount of the material does not, however, prevent the reaction from proceeding.

Among the above-described materials promoting the above reaction, an alkyl halide gives particularly excellent results and the yield for the product is almost quantitative. When an alkylating agent such as an alkyl halide, is employed, the alkyl halide is consumed by the reaction, but because the same amount of an alkyl halide is reproduced at the same time the alkyl halide is consumed, the alkyl halide, supplied to the reaction is completely recovered without being consumed.

When the above-described materials promoting the reaction are used, the reaction is effected at a temperature of from 20°C to 250°C, and preferably from 20°C to 150°C.

Then, of the desired compounds of the present invention, the compound represented by the general formula (I) in which $R_1$ is a hydrogen atom is also prepared from the compound having the general formula (I) in which $R_1$ is a lower alkyl group by subjecting the compound to hydrolysis. The hydrolysis of the derivative can be conducted by reacting the derivative with water but any other technique employed in conventional hydrolysis can be used. For example, when the hydrolysis is conducted in the presence of an alkali metal hydroxide or a mineral acid, such as sulfuric acid or hydrochloric acid, the reaction is quite rapid and in addition, the reaction can be conducted economically.

As discussed above, the process of the present invention is superior to conventional processes in that an expensive reagent, such as an alkyl halide is not consumed or lost in the reaction, the reaction proceeds smoothly, and the desired compound is obtained in high yield.

The compounds of the present invention represented by the general formula (I) exhibit marked antibacterial or central nervous system stimulating activities, and hence are useful as medicaments.

Illustrative of the compounds having the general formula (I) prepared by the process of the present invention, without limiting the generality of the invention, include the following known compounds: 1-ethyl-4-oxo-1,8-naphthyridine-3-carboxylic acid or a methyl ester thereof; 1-ethyl-7-methyl-4-oxo-1,8-naphthyridine-3-carboxylic acid or an ethyl ester thereof; 1-ethyl-5,7-dimethyl-4-oxo-1,8-naphthyridine-3-carboxylic acid or an ethyl ester thereof; 1-ethyl-6-bromo-4-oxo-1,8-naphthyridine-3-carboxylic acid or an ethyl ester thereof; 1-ethyl-7-benzyl-4-oxo-1,8-naphthyridine-3-carboxylic acid or an ethyl ester thereof; 1-ethyl-7-hydroxymethyl-4-oxo-1,8-naphthyldine-3-carboxylic acid or an ethyl ester thereof; 1-ethyl-7-acetyloxymethyl-4-oxo-1,8-naphthyridine-3-carboxylic acid or an ethyl ester thereof; 1-propyl-7-methyl-4-oxo-1,8-naphthyridine-3-carboxylic acid or an ethyl ester thereof; 1-pentyl-7-methyl-4-oxo-1,8-naphthyridine-3-carboxylic acid or an ethyl ester thereof; 1-allyl-7-methyl-4-oxo-1,8-naphthyridine-3 carboxylic acid or an ethyl ester thereof; 1-(2-hydroxymethyl)-7-methyl-4-oxo-1,8-naphthyridine-3-carboxylic acid or an ethyl ester thereof; 1-cyclopropylmethyl-7-methyl-4-oxo-1,8-naphthyridine-3-carboxylic acid or an ethyl ester thereof; 1-ethyl-4-oxo-1,8-naphthyridine-3,7-dicarboxylic acid or an ethyl ester thereof; 1-ethyl-4-oxo-7-styryl-1,8-naphthyridine-3-carboxylic acid or an ethyl ester thereof; 1-ethyl-7-phenethyl-4-oxo-1,8-naphthyridine-3-carboxylic acid or an ethyl ester thereof; and 1-ethyl-7-tribromomethyl-4-oxo-1,8-naphthyridine-3-carboxylic acid or an ethyl ester thereof; 1-ethyl-6,7-methylenedioxy-4-quinolone-3-carboxylic acid or an ethyl ester thereof; 1-ethyl-6,7-ethylenedioxy-4-quinolone-3-carboxylic acid or an ethyl ester thereof; 1-ethyl-6,7-trimethylenedioxy-4-quinolone-3-carboxylic acid or an ethyl ester thereof; 1-ethyl-7,8-methylenedioxy-4-quinolone-3-carboxylic acid and an ethyl ester thereof.

The following novel compounds are alos included without limiting the scope of the present invention: 1-ethyl-6-methoxy-4-quinolone-3-carboxylic acid or an ethyl ester thereof; 1-ethyl-8-methyl-4-quinolone-3-carboxylic acid or ethyl ester thereof; 1-ethyl-6-methyl-4-quinolone-3-carboxylic acid or an ethyl ester thereof; 1-ethyl-8-trifluoromethyl-4-quinolone-3-carboxylic acid or an ethyl ester thereof; 1-ethyl-8-methylmercapto-4-quinolone-3-carboxylic acid or an ethyl ester thereof; 1-ethyl-5-nitro-4-quinoline-3-carboxylic acid or an ethyl ester thereof.

The starting material used in the preparation of the above-described 1-substituted 4-oxo derivative, i.e., the 4-alkyloxy derivative represented by the general formula (III) or the compound of the general formula (II) in which A is OR is a novel compound is prepared by reacting a 4-halogeno derivative represented by the general formula:

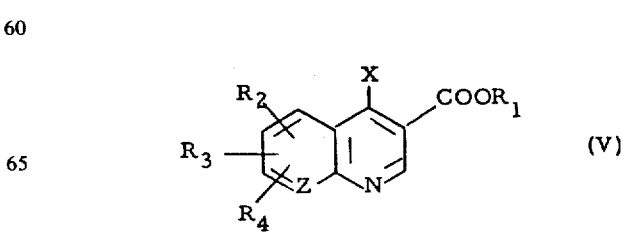

(V)

wherein X represents a halogen atom; $R_1$ represents a lower alkyl group and Z, $R_2$, $R_3$ and $R_4$ are as defined in the general formula (I), with an alcohol represented by the general formula:

ROH wherein R represents a lower alkyl group, a lower alkenyl group, a cycloalkyl group, or a lower hydroxyalkyl group, or further hydrolyzing the product. In this case, it is better to conduct the reaction in the presence of an acid acceptor.

Suitable acid acceptors which can be used in this reaction are inorganic or organic basic materials, such as an alkali metal hydroxide, an alkali metal carbonate, an alkali metal bicarbonate, a metal salt of an alcohol represented by the formula ROH, in which R has the same meanings as above. Pyridine can also be used. However, the use of the metal salt of an alcohol is most preferred. Moreover, in order that the reaction proceeds smoothly, a solvent can be employed. Illustrative of such solvents are solvents which are inert to the reaction, such as benzene, toluene, petroleum benzene, and ether. Additionally, the alcohol represented by the abovedescribed general formula, ROH, can be used. When a large amount of such an alcohol is used, sometimes an ester-exchange reaction of the alkoxycarbonyl group at the 3-position occurs and results in the formation of the 4-alkyloxy ester having the general formula (III) in which $R_1$ is the same lower alkyl group as R.

Also, when the reaction is conducted in the presence of the acid acceptor, sometimes, when $R_2$, $R_3$, and/or $R_4$ are a lower alkylacyloxy group, the lower acyloxy group is hydrolyzed into a hydroxyalkyl group and in such cases it is necessary to use an acid acceptor in an amount greater than 1 mole.

The reaction of present invention can proceed even at low temperatures but can be conducted by heating the system to temperatures of lower than 200°C. Furthermore, when a sodium salt or a potassium salt of the alcohol (ROH) is used, the reaction can proceed at temperatures lower than room temperature with better results.

Then, the compound represented by the general formula (III), wherein $R_1$ is a hydrogen atom, can be obtained by further subjecting the 4-alkyloxy ester prepared as above to hydrolysis. In the hydrolysis, any conventional means can be employed. It is economically profitable to use alkali metal hydroxide as the alkali or a mineral acid, such as sulfuric acid or hydrochloric acid, as the acid. However, not only can inorganic acids or bases be used, but also organic acids or bases as well. Also, the hydrolysis can proceed only in the presence of water without using an acid or a base. The solvent used in the reaction can be water or a solvent, which is miscible with water, such as an alcohol or dioxane.

Moreover, the 4-halogeno ester, which is the starting material having the general formula (V) used for producing the 4-alkyloxy derivative as described above is also a novel compound and the compound is produced by reacting a 4-hydroxy compound represented by the general formula:

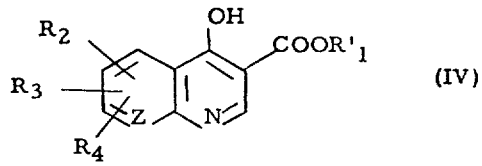

(IV)

wherein $R'_1$ represents a lower alkyl group; Z, $R_2$, $R_3$ and $R_4$ have the same meanings as in the above-described general formula (I), with a halogenating agent, such as phosphorus oxychloride, phosphorus oxybromide, phosphorus pentachloride, phosphorus trichloride, phosgene, or mixtures thereof.

The above reaction can proceed even at low temperatures but good results are obtained when the reaction system is heated preferably to a temperature of from 30°C to 100°C. Further, the reaction can be conducted at temperature of from 100°C to 200°C, but in general, the yield of the product tends to be reduced when a reaction temperature of higher than 150°C is used. The reaction can proceed in the absence of a solvent but the reaction can be carried out smoothly in a solvent, which is inert to the reaction, such as toluene, benzene, chlorobenzene, dichloroethane, chloroform, ether, and a petroleum hydrocarbon. Furthermore, an excess amount of halogenating agent can be used as the solvent for these purposes. To promot the reaction, a compound such as pyridine, diethylamine, dimethylformamide can be present in the reaction system.

Furthermore, the 4-halogeno-3-quinoline carboxylic acid ester, which is represented by the general formula (V), wherein Z represents CH, and X, $R_1$, $R_2$, $R_3$ and $R_4$ have the same meanings as defined above, can be prepared by reacting an alkylenedioxyanilinomethylenemalonic acid ester with a halogenating agent. A chlorine atom, a bromine atom, and an iodine atom are included as the halogen atoms in these compounds.

The present invention will be explained in greater detail by reference to the following examples, but these examples are not to be interpreted as limiting.

EXAMPLE 1

A mixture of 10 g of ethyl 4-hydroxy-7-methyl-1,8-naphthyridine-3-carboxylate and 50 ml of phosphorus oxychloride was heated at 60°C with stirring for 1 hour. The excess phosphorus oxychloride was removed under reduced pressure and the product was poured into ice-water. The insoluble matter was filtered off, the filtrate was adjusted to pH 8 by the addition of aqueous ammonia under cooling and extracted with ether. The extracts were dried over anhydrous magnesium sulfate. Then 0.5 g of activated carbon was added to the ether extracts for decoloration. The ether extracts were filtered, concentrated to a small volume and cooled. The precipitate was filtered to provide 8.6 g of ethyl 4-chloro-7-methyl-1,8-naphthyridine-3-carboxylate as yellow needles, m.p. 99°–100°C (decomp.).

Elementary %; Calculated for $C_{12}H_{11}N_2O_2Cl$: C 57.49%, H 4.42%, N 11.18%, Cl 14.14% Found: C 57.46%, H 4.48%, N 11.26%, Cl 13.88%.

EXAMPLE 2

To 17 ml of ethanol was added 4.26 g of ethyl 4-chloro-7-methyl-1,8-naphthyridine-3-carboxylate followed by a sodium ethylate solution prepared from 0.39 g of metallic sodium and 12 ml of ethanol under cooling over a period of 10 minutes. The mixture was stirred at room temperature for 1 hour. The ethanol was removed under reduced pressure, the residue was dissolved in chloroform, the chloroform solution was washed with water to remove the inorganic salts, and dried over magnesium sulfate.

The chloroform was distilled off under reduced pressure, and the residue was recrystallized from petroleum benzine to provide 4.1 g of ethyl4-ethoxy-7-methyl-1,8-naphthyridine-3-carboxylate appearing as colorless needles, m.p. 82°–83°C.

Elementary Analysis: Calculated for: $C_{14}H_{16}C_3N_2$: C 64.60%, H 6.20%, N 10.76%; Found: C 64.58%, H 6.27%, N 10.85%.

EXAMPLE 3

A mixture containing 1.8 g of ethyl 4-ethoxy-7-methyl-1,8-naphthyridine-3-carboxylate and 15 g of ethyl iodide was refluxed for 1 hour on a water bath. The ethyl iodide was removed by distillation and the residue was recrystallized from isopropyl ether or ethyl acetate-n-hexane to provide 1.6 g of colorless needles of ethyl -1-ethyl-7-methyl-4-oxo-1,8-naphthyridine-3-carboxylate, m.p. 122.5°–123.5°C. The product was confirmed by mixed melting point determination and comparison of the IR spectrum with that of an authentic specimen.

Elementary Analysis Calculated for: $C_{14}H_{16}C_3N_2$: C 64.60%, H 6.20%, N 10.76%; Found: C 63.39%, H 6.31%, N 10.44%.

EXAMPLE 4

A mixture containing 1.63 g of ethyl 4-ethoxy-7-methyl-1,8-naphthyridine-3-carboxylate and 15 g of ethyl iodide was refluxed for one hour on a water bath. After the ethyl iodide was distilled off, 15 ml of 5% aqueous potassium hydroxide solution was added to the residue and the resulting mixture was heated with stirring for 2 hours on a boiling water bath.

The mixture was treated with 0.2 g of activated carbon and the filtrate was adjusted to a pH of 3–4 by the addition of 6 N hydrochloric acid. The precipitate was filtered, washed with water and dried to provide 1.3 g of pure 1-ethyl-7-methyl-4-oxo-1,8-naphthyridine-3-caboxylic acid having a melting point of 224°–225°C. The sample was recrystallized from dimethy formamide-water to yield the compound as colorless needles. The product was confirmed by mixed melting point determination and comparison of the IR spectrum with that of an authentic specimen.

Elementary Analysis Calculated for: $C_{12}H_{13}O_3N_2$: C 62.06%, H 5.21%, N 12.06%; Found: C 62.30%, H 5.15%, N 12.13%.

EXAMPLE 5

After heating 0.2 g of ethyl 4-ethoxy-7-methyl-1,8-naphthyridine-3-carboxylate for 3 hours on an oil bath of 155°–160°C, the reaction product was dissolved in chloroform and the solution was passed through a column packed with silica gel to decolor the solution. The chloroform was distilled from the elutate and the residue was recrystallized to provide ethyl 1-ethyl-7-methyl-4-oxo-1,8-naphthyridine-3-carboxylate having a melting point of 122°–123°C.

EXAMPLE 6

A mixture containing 1 g of ethyl 4-ethoxy-7-methyl-1,8-naphthyridine-3-carboxylate, 1.26 g of ethyl bromide and 20 ml of toluene was heated in a sealed tube at 130°C for 7 hours. The solvent was evaporated and the residue was worked up as above. There was obtained 0.8 g of ethyl-1-ethyl-7-methyl-4-oxo-1,8-naphthyridine-3-carboxylate.

EXAMPLE 7

A mixture containing 30 g of diethyl 3,4-methylenedioxyanilinomethylene malonate and 240 ml of phosphorus oxychloride was heated at 95°C with stirring for 3.5 hours. Then, excessive phosphorus oxychloride was concentrated under reduced pressure. The residue was poured into ice-water, the solution was neutralized with aqueous sodium carbonate solution and the yellow crystalline precipitate which deposited was collected by filtration, washed with water, and dried. There was obtained 26.2 g of ethyl 4-chloro-6,7-methylenedioxyquinoline-3-carboxylate. Recrystallization from ethanol gave light yellow rhombs, m.p. 109°–109.5°C.

Elementary Analysis: Calcualted for: $C_{13}H_{10}NO_4Cl$: C 55.86%, H 3.60%, N 5.01%; Found: C 55.69%, H 3.33%, N 5.00%.

EXAMPLE 8

To a mixture containing 126 g of ethyl 4-chloro-6,7-methylenedioxyquinoline-3-carboxylate and 200 ml of absolute ethanol was added dropwise an ethanolic sodium ethylate solution prepared from 34 g of sodium ethylate and 250 ml of ethanol with stirring. The resulting mixture was refluxed for 1.5 hours and the ethanol was removed under reduced pressure. The residue was poured into ice-water, the insoluble solid was filtered, washed with water and dried to provide 126 g of almost pure ethyl 4-ethoxy-6,7-methylenedioxyquinoline-3-caboxylate, m.p. 84°–86°C. Recrystallization from petroleum ether gave colorless needles, m.p. 85°–85.5°C.

Elementary Analysis: Calculated for: $C_{15}H_{15}O_5N$: C 62.28%, H 5.23%, N 4.84%; Found: C 62.35%, H 5.24%, N 4.84%.

EXAMPLE 9

A mixture containing 25 ml of toluene, 5 g of ethyl 4-ethoxy-6,7-methylenedioxyquinoline-3-carboxylate and 0.9 g of ethyl iodide was heated at 160°C for 40 hours. After cooling, ethyl 1-ethyl-6,7-methylenedioxy-4-quinolone-3-carboxylate which precipitated was collected by filtration, washed with toluene and dried. The product weighed 4.95 g and melted at 177°–178°C. No depression of the melting point was observed when admixed with an authentic sample of the ester and the IR spectra of the two samples were identical.

The ethyl 1-ethyl-6,7-methylenedioxy-4-quinolone-3-carboxylate thus obtained was heated at 90°–100°C for 30 minutes together with 50 ml of a 5% aqueous sodium hydroxide solution and then the pH of the solution was adjusted to 2 with hydrochloric acid, whereby a crystalline precipitate was formed, which was collected by filtration, washed with water and dried. The melting point of the product was 318°C (decomposed). The infrared absorption spectrum of the product was identical with that of an authentic sample of 1-ethyl-6,7-methylenedioxy-4-quinolone-3-carboxylic acid. Yield: 4.43 g

EXAMPLE 10

A mixture containing 25 ml of toluene, 5 g of ethyl 4-ethoxy-6,7-methylenedioxyquinoline-3-carboxylate and 5.67 g of ethyl bromide was placed in a sealed tube and heated at 130°C (bath temperature) for 30 hours. The reaction mixture was worked up as described in Example 9 and 4.93 g of ethyl 1-ethyl-6,7-methylenedioxy-4-quinolone-3-carboxylate was obtained.

EXAMPLE 11

A mixture containing 2.75 g of methyl 4-methoxy-6,7-methylenedioxyquinoline-3-carboxylate and 10 ml of methyl iodide was refluxed for 30 minutes. The product was diluted with toluene, cooled, and methyl 1-methyl-6,7-methylenedioxy-4-quinolone-3-carboxylate thus precipitated was collected by filtration. The melting point thereof was 185°–186°C.

Elementary Analysis: Calculated for: $C_{14}H_{13}C_5N$: C 61.09%, H 4.7%, N 5.09%; Found: C 61.22%, H 4.7%, N 5.15%.

EXAMPLE 12

A melt of 5 g of ethyl 4-ethoxy-6,7-methylenedioxyquinoline-3-carboxylate was heated at 220°C for 7 hours and then cooled. The product was thinned with toluene, filtered and recrystallized from chloroform petroleum ether to provide 3.7 g of ethyl 1-ethyl-6,7-methylenedioxy-4-quinolone-3-carboxylate as needles, m.p. 177°–178°C.

EXAMPLE 13

A mixture of 2.9 g of ethyl 4-ethoxy-6,7-methylenedioxyquinoline 3-carboxylate and 0.03 g of p-toluenesulfonic acid was melted and heated at 180°C (bath temperature) for 2 hours and cooled. The product was dissolved in chloroform, washed with a dilute aqueous sodium carbonate solution and then with water. The chloroform layer was separated and evaporated to dryness. There was obtained 2.85 g of pure ethyl 1-ethyl-6,7-methylenedioxy-4-quinolone-3-carboxylate, m.p. 175°–177°C.

EXAMPLE 14

A mixture of 5 g of ethyl 4-ethoxy-6,7-methylenedioxyquinoline-3-carboxylate and 0.06 g of p-toluenesulfonic acid was heated at 180°C for 3 hours and cooled. To the product was added 50 ml of a 5% aqueous sodium hydroxide solution. The resulting mixture was heated at 90°–100°C for 30 minutes, the acidified by the addition of dilute hydrochloric acid and cooled. The precipitate was collected by filtration, washed with water and dried. There was obtained 4.42 g of 1-ethyl-6,7-methylenedioxy-4-quinolone-3-carboxylic acid, m.p. 318°C (decomposition).

By the similar procedure described above, the following 1-substituted-4-quinolone-3-carboxylates were prepared:

1-Ethyl-6-methoxy-4-quinolone-3-carboxylic acid, m.p. 218.5–219°C, and its ethyl ester, m.p. 147°–148°C.

1-Ethyl-8-methyl-4-quinolone-3-carboxylic acid, m.p. 202°–205°C, and its ethyl ester, 128°–129°C.

1-Ethyl-6,7-dimethoxy-4-quinolone-3-carboxylic acid; m.p. 255.5°–256°C, and its ethyl ester, m.p. 154.5°–156.5°C.

1-Ethyl-6-methyl-4-quinolone-3-carboxylic acid, 218.5°–219.5°C.

1-Ethyl-7,8-cyclopentano-4-quinolone-3-carboxylic acid, m.p. 270+–271°C.

1-Propyl-7,8-cyclopentano-4-quinolone-3-carboxylic acid, m.p. 267°–269°C.

1-Ethyl-6,7-cyclopentano-4-quinolone-3-carboxylic acid, m.p. 290°C, and its ethyl ester, m.p. 286°C.

1-Ethyl-6,7-ethylenedioxy-4-quinolone-3-carboxylic acid, m.p. 255°–257°C (decomp.), and its ethyl ester, m.p. 185°–187°C.

EXAMPLE 15

To 80 ml of methanol containing 1.4 g of sodium methylate having a purity of 97% was added 7 g of ethyl 4-chloro-6,7-methylenedioxyquinoline-3-carboxylate and the mixture was refluxed for 30 minutes. After the methanol was distilled off, the residue was washed with water and filtered. The product was dried and recrystallized from ethyl acetate to provide 6 g of methyl 4-methoxy-6,7-methyldioxyquinoline-3-carboxylate as colorless needles, m.p. 148°–149°C.

Elementary Analysis: Calculated for: $C_{13}H_{11}O_5N$: C 59.77%, H 4.24%, N 5.36%; Found: C 59.65%, H 4.33%, N 5.38%.

EXAMPLE 16

To a mixture containing 6.1 g of ethyl 4-chloro-6,7-methylenedioxyquinoline-3-carboxylate and 20 ml of isopropanol was added dropwise an isopropanolic solution of sodium isopropoxide prepared from 0.55 g of metallic sodium and 20 ml of isopropanol. The resulting mixture was refluxed for 40 minutes, the isopropanol was distilled off, the residue was poured into water and extracted with ether. The ether extracts were dried over anhydrous sodium sulfate, and evaporated to provide a viscous oil, which was confirmed to be isopropyl 4-isopropoxy-6,7-methylenedioxyquinoline-3-carboxylate by measurement of the nuclear magnetic resonance spectrum. The yield was 6 g. A part of the product was converted into the picrate. The product appeared as yellow needles, m.p. 174°C (decomposition).

Elementary Analysis: Calculated for: $C_{23}H_{22}O_{12}N_4$: C 50.55%, H 4.06%, N 10.25% Found: C 50.30%, H 4.08%, N 10.14%.

EXAMPLE 17

To 120 ml of 5% ethanolic sodium hydroxide solution was added 6 g of ethyl 4-ethoxy-6,7-methylenedioxyquinoline-3-carboxylate with stirring, and the mixture was stirred further for 15 minutes at room temperature then concentrated to a small volume under reduced pressure. A small amount of water was added to the residue, the pH of the solution was adjusted to 5 by the addition of hydrochloric acid, and the precipitate thus formed was filtered, washed with water and dried to provide 5.2 g of almost pure 4-ethoxy-6,7-methylenedioxyquinoline-3-caboxylic acid having a melting point of 250°–253°C. Recrystallization from dimethyl sulfoxide gave colorless needles having a melting point of 252°C (decomposed).

Elementary Analysis: Calculated for: $C_{13}H_{11}O_3N$: C 59.77%, H 4.24%, N 5.34%; Found: C 59.51%, H 4.05%, N 5.36%.

EXAMPLE 18

A mixture containing 1 g of 4-ethoxy-6,7-methylenedioxyquinoline 3-carboxylic acid, 10 ml of ethyl iodide and 10 ml of dimethylformamide was placed in a sealed tube and heated at 80°–100°C (bath temperature) for 5 hours. Excess ethyl iodide was recovered by distillation, 40 ml of water was added to the residual solution and the insoluble 1-ethyl-6,7-methylenedioxy-4-quinolone-3-carboxylic acid was collected by filtration, washed with water and dried. The yield was 0.9 g, m.p. 295°–300°C (decomposition). Recrystallization from dimethylformamide afforded colorless needles, m.p. 318°C (decomposition).

Although the present invention has been adequately set forth in the specification and examples included therein, one readily realizes that various changes and modifications can be made without departing from the scope thereof.

Further regarding the antibacterial activity of the compounds of the present invention, they are especially effective in treating gram negative bacterial infections of the urinary and intestinal tract, as well as certain gram positive organisms. Illustrative of these gram negative and positive organisms are E. Col.1, Proteus mirabillis, Klebsiella pneumonia and Staphylococcus aureus.

What is claimed is:

1. A process for the production of a 1,4-dihydro-7-methyl-4-oxo-1,8-naphthyridine-3-carboxylic acid represented by the formula I

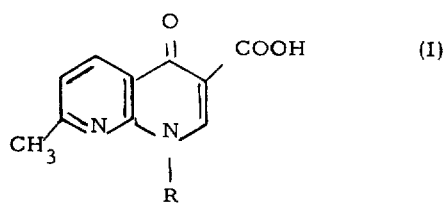

wherein R is a $C_1-C_4$ alkyl group, which process comprises a. reacting the compound represented by the formula II

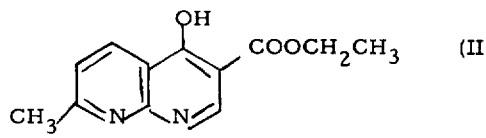

with a halogenating agent to provide the compound represented by the formula III

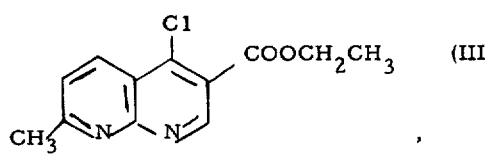

b. reacting the compound III so formed in the presence of a base selected from the group consisting of an alkali metal hydroxide, an alkali metal carbonate, a metal salt of an alcohol represented by the formula ROH wherein R is as described above and pyridine with an alcohol represented by the formula

ROH wherein R is as described above, to provide a compound represented by the formula IV

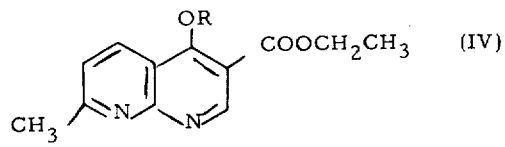

wherein R is as described above:

c. heating the compound IV in the presence of absence of an alkylating agent or an acid to provide a compound represented by the formula V, wherein said alkylating agent is an alkyl halide, an alkenyl halide, an alkyl p-toluene sulfonate, a cycloalkyl halide, an hydroxy alkyl halide, a dialkyl sulfate or triethyloxonium fluoroborate and wherein said acid is a strong, non- oxidizing inorganic or organic acid or a Lewis acid

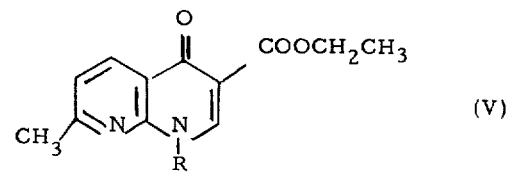

and d. then hydrolyzing the compound V to provide a 1,4-dihydro-7-methyl-4-oxo-1,8-naphthyridine-3-caboxylic acid represented by the formula I.

2. The process of claim 1 wherein process step (c) is carried out by heating compound (IV).

3. The process of claim 1 wherein process step (c) is carried out in the presence of an acid catalyst and in the absence of an alkylating agent.

4. The process of claim 1 wherein process step (c) is carried out in the presence of an alkylating agent and in the absence of an acid catalyst.

5. The process of claim 1 wherein the base utilized in process step (b) is an alkali metal hydroxide.

6. The process of claim 1 wherein the base utilized in process step (b) is an alkali metal carbonate.

7. The process of claim 1 wherein the alkylating agent is used in process step (c), said alkylating agent being a lower alkyl halide.

8. The process of claim 1 wherein the alkylating agent is used in process step (c), said alkylating agent being a lower alkyl sulfate.

9. The process of claim 1 wherein an acid is used in process step (c), said acid being an organic acid.

10. The process of claim 1 wherein an acid is used in process step (c), said acid being a Lewis acid.

11. The process of claim 1 wherein the product of each of steps (a), (b) and (c) is isolated prior to proceeding with the next step of the process.

* * * * *